United States Patent [19]

Ahmed et al.

[11] Patent Number: 5,866,675
[45] Date of Patent: *Feb. 2, 1999

[54] NONWOVEN WEB COMPRISING WATER SOLUBLE POLYAMIDES AND ARTICLES CONSTRUCTED THEREFROM

[75] Inventors: Sharf U. Ahmed, Woodbury; Greg J. Van Lith, Fridley, both of Minn.

[73] Assignee: H. B. Fuller Licensing & Financing, Inc., St. Paul, Minn.

[ * ] Notice: The term of this patent shall not extend beyond the expiration date of Pat. No. 5,663,286.

[21] Appl. No.: 927,116

[22] Filed: Aug. 29, 1997

Related U.S. Application Data

[63] Continuation-in-part of Ser. No. 555,524, Nov. 9, 1995, Pat. No. 5,663,286.

[51] Int. Cl.$^6$ .................................................. C08G 69/26
[52] U.S. Cl. .......................... 528/339; 528/310; 528/335; 528/338; 528/339.3; 528/340; 528/347; 428/474.5; 604/358
[58] Field of Search .................................. 528/310, 335, 528/339, 338, 339.3, 340, 347; 428/474.5; 604/358

[56] References Cited

U.S. PATENT DOCUMENTS

| | | | |
|---|---|---|---|
| 3,882,090 | 5/1975 | Fagerberg et al. | 528/339 |
| 5,053,484 | 10/1991 | Speranza | 528/338 |
| 5,086,162 | 2/1992 | Speranza et al. | 528/339 |
| 5,118,785 | 6/1992 | Speranza et al. | 528/338 |
| 5,324,812 | 6/1994 | Speranza et al. | 528/325 |
| 5,663,286 | 9/1997 | Ahmed et al. | 528/339 |

FOREIGN PATENT DOCUMENTS

WO96/08538  3/1996  WIPO.

OTHER PUBLICATIONS

*DEVELOPMENT and EVALUATION OF WATER SOLUBLE MELT BLOWN NONWOVENS*, Denver, Benson, and Pair, INDA JNR, vol. 5, No. 2, (1993), pp. 27–33.
Texaco Chemical Company, Jeffamine Amines–Polyamides from Polyoxyethylene Diamines, Nov. 3, 1992, Prepared by George Speranza and Chris Henkee.

*Primary Examiner*—P. Hampton-Hightower
*Attorney, Agent, or Firm*—Nancy N. Quan; Carolyn A. Fischer

[57] ABSTRACT

This invention relates to a nonwoven web comprising a water soluble polyamide and articles constructed therefrom. The water soluble polyamide may be used alone or in combination with conventional thermoplastic web forming materials such as water insoluble polyethylene, polypropylene, polyester and polyamide. The water soluble polyamide may also be combined with biodegradable or selectively dispersible material to form nonwoven webs having various combinations of properties. Such water soluble webs have utility in the manufacture of disposable absorbent articles such as disposable diapers, feminine napkins, incontinent products and cellulosic articles such as tissues and towels, as well as for water soluble heat fusible webs for the textile industry.

17 Claims, No Drawings

//5,866,675

NONWOVEN WEB COMPRISING WATER SOLUBLE POLYAMIDES AND ARTICLES CONSTRUCTED THEREFROM

RELATED APPLICATIONS

This application is a Continuation-In-Part of Ser. No. 08/555,524 filed Nov. 9, 1995 now U.S. Pat. No. 5,663,286.

FIELD OF THE INVENTION

This invention relates to a nonwoven web comprising a water soluble polyamide and articles constructed therefrom. The invention further relates to a method of using certain water soluble polyamides for producing a water soluble or water dispersible web. The water soluble polyamide may be used alone or in combination with conventional thermoplastic web forming materials such as water insoluble polyethylene, polypropylene, polyester and polyamide. The water soluble polyamide may also be combined with biodegradable or selectively dispersible material to form nonwoven webs having various combinations of properties. Such water soluble webs have utility in the manufacture of disposable absorbent articles such as disposable diapers, feminine napkins, incontinent products and cellulosic articles such as tissues and towels, as well as for water soluble heat fusible webs for the textile industry.

BACKGROUND OF THE INVENTION

Melt blown and spunbond webs typically comprise insoluble and nondegradable polymers such as water insoluble polyethylene, polypropylene, polyester and polyamide. Such webs are used in the manufacture of a variety of disposable products such as disposable diapers, feminine napkins, surgical gowns, laundry bags, bed pads, and the like. Such articles are designed to absorb and contain bodily fluids and/or provide a physical barrier to such fluids. Water soluble and biodegradable nonwoven webs may provide some solutions to environmental concerns regarding the disposal of such items.

Heat fusible webs are used for a variety of uses. In the textile industry, heat fusible webs are used to hold pieces of fabric, such as a patch pocket, in place prior to being sewn. These heat fusible webs are also used to create hems on pants or for a variety of ornamental craft appliqués. Webs currently available for such uses are typically low viscosity at application temperature and insoluble in water. Upon activation with heat these materials often soak into the fabric workpiece causing the fabric to become stiff. Often the melted web soaks in to the extent that it fails to form the intended bond and reapplication is necessary.

A water soluble nonwoven comprising polyvinyl alcohol (PVOH) is taught in Dever et al., JP 59041260. Modifying the rate of water solubility of a PVOH based melt blown material using two different chemical treatments is described in the *Development and Evaluation of Water Soluble Melt Blown Nonwovens*, Dever, Benson, and Pair, INDA JNR, Vol. 5, No. 2, published 1993.

PVOH as a base polymer for the formation of a water soluble web suffers from several disadvantages. Due to its high melt point and poor thermal stability, it is very difficult to thermally process. An extruder, rather than merely a melt tank, is required to process the PVOH into a web. Additionally, once the web is formed, it has poor heat seal properties such that it would need to be heat sealed at temperatures that adversely affect the integrity of the substrate.

Water soluble polyamides prepared from an aliphatic dicarboxylic acid, a modifying acid, and an aliphatic diamine are reported by Fagerberg et al., U.S. Pat. No. 3,882,090. The polyamides are useful as textile sizing agents, coatings, and adhesives. Column 4, lines 28–33 states, "The various methods of preparing polyamides are well known in the art as well as a number of polymers which contain ether linkages in the polymer chain. These however, are basically fiber forming polyamides and therefore not contemplated by the present invention."

Speranza et al., U.S. Pat. Nos. 5,053,484; 5,086,162; 5,324,812 and 5,118,785 are directed to certain polyamides having good water absorbency for use as fibers. Collectively, the polyamides taught therein either exhibit a high melt point, much like the PVOH, requiring an extruder for processing into a nonwoven web, or in the case of those polyamides having lower melt points, are disadvantageous in that the polyamides, once formed into a nonwoven web, tend to block. At column 1, lines 21–16 the 5,324,812 patent discusses that several nylon manufacturers incorporate polyoxyalkyleneamines into their products to modify the final properties. The polyether backbone of these components improves the comfort feel, wickability and dyeability of textile grades. However, no such compositions have been used to form a water soluble nonwoven web.

The applicants have found that certain water soluble polyamides exhibit proved melting characteristics for manufacturing spunbond and melt blown nonwoven webs. Further, the resulting webs are water soluble, humidity resistant and nonblocking, meaning the web can be rolled upon itself and subsequently unwound without adjacent layers adhering to each other.

SUMMARY OF THE INVENTION

The present invention discloses a water soluble nonwoven web comprising a polyamide and articles constructed therefrom. The invention further relates to method a of using certain polyamides to form a water soluble or water dispersible nonwoven web. The polyamide is water soluble and selected from the group consisting of:

a) the reaction product of at least one dicarboxylic acid or an ester thereof with a polyalkylene glycol diamine having the formula:

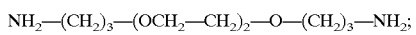
$NH_2-(CH_2)_3-(OCH_2-CH_2)_2-O-(CH_2)_3-NH_2;$ b) the reaction product of at least one polyalkylene glycol diamine with at least one dicarboxylic acid or an ester thereof, and at least one monocarboxylic acid and/or monoamine, said polyalkylene glycol diamine having the formula:

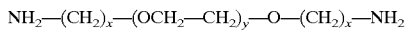
$NH_2-(CH_2)_x-(OCH_2-CH_2)_y-O-(CH_2)_x-NH_2$ wherein X ranges from 2 to 3 and Y ranges from 1 to 2;

c) up to about 99 wt-% of the reaction product of at least one polyalkylene glycol diamine with at least one dicarboxylic acid or an ester thereof, said polyalkylene glycol diamine having the formula:

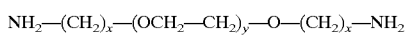
$NH_2-(CH_2)_x-(OCH_2-CH_2)_y-O-(CH_2)_x-NH_2$ wherein X ranges from 2 to 3 and Y ranges from 1 to 2; and about 1 to about 50 wt-% of at least one ingredient selected from the group consisting of waxes, tackifiers, crystalline polymers, monocarboxylic acids, monoamines and mixtures thereof.

The water soluble polyamide may be a single polyamide produced from each of the distinct categories described above or a mixture of such polyamides. The resulting web produced from such polyamides is nonblocking and humidity resistant.

The water soluble polyamide may be used alone or in combination with conventional thermoplastic web forming materials such as water insoluble polyethylene, polypropylene, polyester and polyamide. The water soluble polyamide may also be combined with biodegradable or selectively dispersible material to form nonwoven webs having various combinations of properties. The nonwoven web may be formed from spunbond and melt blown techniques as well as be sprayed molten or in an aqueous dispersion form.

Furthermore, the polyamide may be sprayed or dispersed in water to be used as a binder bonding fiber in air laid or wet laid processes. This aspect is particularly useful for improving the strength of cellulosic absorbent products such as tissues and towels.

The resulting nonwoven can be used to form laminates such as those found in disposable articles to incorporate hydrophilic and water soluble features into the product. Such water sensitivity may facilitate recycling and composting efforts related to solid waste management as well as improve fluid transfer and acquisition. Additionally, nonwoven webs comprising a water soluble polyamide are useful for making water soluble heat fusible webs. A 4,7,10 trioxatridecane-1,13-diamine is preferred due to its low melt temperature. Since the resulting web will dissolve during washing, such a web will overcome the problems of insoluble heat fusible webs used for temporary bonding in the textile industry.

DETAILED DESCRIPTION OF THE INVENTION

The present invention is a nonwoven web comprising a water soluble polyamide. The resulting web is water soluble or water dispersible. Such polyamides are the reaction product of at least one polyalkylene glycol diamine with at least one dicarboxylic acid or esters thereof.

The polyalkylene glycol diamine has the formula:

$$NH_2-(CH_2)_x-(OCH_2-CH_2)_y-O-(CH_2)_x-NH_2$$

wherein X ranges from 2 to 3 and Y ranges from 1 to 2.

Representative examples include triethylene glycol diamine, wherein X=2 and Y=1, and tetraethylene glycol diamine, wherein X=2 and Y=2. Commercial diamines include Jeffamine® 148 amine and Jeffamine® 192 amine available from Huntsmen Chemical Co., Houston, Tex. A preferred diamine is 4,7,10 - trioxatridecane-1,13-diamine (TTD diamine) available from BASF, Parsippany, N.J., wherein X=3 and Y=2. Other amines such as Jeffamine® D-230, D-400, ED-600, ED-900, and ED-2000 are also useful provided a chain terminator acid is employed during the reaction and/or additional ingredients such as waxes, tackifiers, crystalline polymers, and monoacids are subsequently combined with the reacted polyamide. For example, when adipic acid is reacted with TTD diamine and Jeffamine® D-230, the resulting polyamide is relatively slow setting with respect to reacting adipic acid with TTD diamine alone.

The polyalkylene glycol diamine is reacted with an equal stochiometric ratio of a dicarboxylic acid. Suitable dicarboxylic acids are those having from 5 to 36 carbon atoms including adipic acid, pimelic acid, azelaic acid, sebacic acid, suberic acid, dodecanedioic acid, terephthalic acid, isophthalic acid, t-butyl isophthalic acid, dimer acid and mixtures thereof. The esters and anhydrides of these acids may also be used. Adipic acid is preferred.

The resulting water soluble polyether amide preferably has a melt point about 190° C. or less as the case when adipic acid is reacted with Jeffamine® 148. More preferably, the melt point is about 155° C. or less as the case when adipic acid is reacted with Jeffamine® 192. The most preferred water soluble polyether amide has a melt point about 150° C. or less as the case when adipic acid is reacted with TTD diamine. This particular combination results in a faster setting, strong, easily processed water soluble polyether amide. The low melt temperature makes this combination particularly preferred for heat fusible webs. Often heat fusing such webs at temperatures above 150° C. adversely affects the integrity of the substrates to be bonded. The resulting web is insoluble in dry cleaning solvent rendering the article (fabric) dry cleanable when necessary.

The applicants have found that certain polyamides may be used alone, uncompounded with additional ingredients, to form a water soluble web that is nonblocking and humidity resistant. Polyamides exhibiting such properties are those which are produced by reacting polyalkylene glycol diamine with at least one dicarboxylic acid or an ester thereof, the polyalkylene glycol diamine having the formula:

$$NH_2-(CH_2)_3-(OCH_2-CH_2)_2-O-(CH_2)_3-NH_2.$$

In this embodiment, adipic acid is the preferred dicarboxylic acid. However, other acids may also be employed provided the mole percent of the additional acids is about 10 mole percent or less with respect to the total acid content. When an additional acid is employed at a concentration greater than about 10 mole percent, particularly at about 25 mole percent or greater with respect to the total acid content, the resulting polyamide exhibits a longer set time prior to becoming completely non-blocking. Accordingly, it is often desirable to add an additional ingredient to increase the rate of set as described in further embodiments as follows.

Additionally, other polyamides are also useful for forming nonblocking, humidity resistant webs provided a chain terminator is employed during the reaction and/or the polyamide is further combined with at least one additional ingredient including waxes, solid tackifiers, monocarboxylic acids, and crystalline polymers. In these embodiments, the polyamide is produced by reacting at least one polyalkylene glycol diamine with dicarboxylic acid or an ester thereof, said polyalkylene glycol diamine having the formula:

$$NH_2-(CH_2)_x-(OCH_2-CH_2)_y-O-(CH_2)_x-NH_2$$

wherein X ranges from 2 to 3 and Y ranges from 1 to 2.

Chain terminators include monoacids and/or monoamines and are useful in an amount less than about 5 wt-%, preferably 0.5–2.5 wt-% based on total acid weight to control the molecular weight. Representative examples of useful monocarboxylic acids include stearic acid, benzoic acid and montannic acid such as Wax S available from Hoechst Celanese. In the absence of a chain terminator, the resulting polyamide, particularly those taught by Speranza in U.S. Pat. Nos. 5,053,484, 5,086,162, 5,324,812, and 5,118,785 are deficient in at least one property including exhibiting a high melt point, slow rate of set, poor humidity resistance, and/or poor blocking resistance.

In addition or in the alternative, the polyamide produced may be combined with at least one ingredient selected from the group consisting of waxes, tackifiers, crystalline polymers, monocarboxylic acids and mixtures thereof. The monocarboxylic acids and monoamines have been found to be useful not only as a reactant as previously described but also as an ingredient to be added after the polyamide is formed.

The additional ingredient necessary to the invention for this embodiment is present in an amount from about 1 wt-% to about 50 wt-%, preferably from about 1 wt-% to about 30 wt-%, and most preferably from about 1 wt-% to about 10 wt-%. Surprisingly as little as 1 wt-% of an additional ingredient, particularly a wax, exhibits a dramatic affect on the blocking resistance of the polyamide. However, if the additional ingredient selected is also water soluble, such ingredient may be present in amounts greater than 50 wt-%.

Waxes useful herein are preferably polar in nature and include representative examples including 12-hydoxysteramide, N-(2-hydroxy ethyl 12-hydroxy steramide (Paracin 220 from CasChem), steramide (Kemamide S from Witco), glycerin monosterate, sorbitan monosterate, and 12-hydoxy stearic acid. Also useful in combination with the above are less polar waxes such as N,N'-ethylene-bis steramide (Kemamide W-40 from Witco), hydrogenated castor oil (castor wax), oxidized synthetic waxes, and functionalized waxes such as oxidized polyethylene waxes (Petrolite E-1040).

Suitable crystalline thermoplastic polymers include ethylene-vinyl acetate copolymers containing about 12 to 50% vinyl acetate, ethylene acrylic acid, ethylene methyl acrylate and ethylene n-butyl acrylate copolymers as well as polylactide, caprolactone polymers, and poly (hydroxybutyrate/hydroxyvalerate), polyvinyl alcohol, linear saturated polyesters such as Dynapol or Dynacoll polymers from Huls, poly (ethylene oxide)polyether amide and polyester ether block copolymers available from Atochem (PeBax) or Hoechst Celanese (Rite-flex) respectively, and polyamide polymers such as those available from Union Camp (Unirez) or Hulls (Vestamelt) or EMS-Chemie (Griltex). The polymers added may be amorphous or crystalline, but at least 5% of a crystalline polymer is required to achieve adequate properties.

Tackifying resins, particularly those having high softening points may be employed to reduce the blocking tendencies. However, in most instances it is necessary to employ a wax and/or crystalline polymer in combination with a tackifying resin to achieve the desired web properties. The tackifying resins useful herein are generally polar in nature and have a Ring & Ball softening point greater than 60° C. and include any compatible resins or mixtures thereof such as natural and modified rosins such as gum rosin, wood rosin, tall oil rosin, distilled rosin, hydrogenated rosin, dimerized rosin, and polymerized rosin; rosin esters such as glycerol and pentaerythritol esters of natural and modified rosins such as for example, the glycerol ester of pale, wood rosin, and the glycerol ester of hydrogenated rosin, the glycerol ester of polymerized rosin, and the pentaerythritol ester of hydrogenated rosin, and the phenolic-modified pentaerytritol ester of rosin; phenolic modified terpene or a-methyl styrene resins as well as the hydrogenated derivatives thereof such as the resin product resulting from the condensation, in an acidic medium of a bicyclic terpene and a phenol.

Representative examples of polar tackifiers include material such as Foral NC available from Hercules; non-ionin materials such as Foral AX also from Hercules, alpha methyl styrene phenolics such as Uratak 68520 from DSM Resins, rosin esters such as Unitac R100L available from Union Camp and terpene phenolic tackifiers such as Nirez 300 and Nirez V2040 available from Arizona Chemical.

It may also be desirable to incorporate up to 20 wt-% of certain hydrophilic non-crystalline polymers such as hydroxyethyl cellulose, hydroxypropyl cellulose, polyvinyl methyl ether, polyvinylpyrrolidone, polyethyloxazoline, starch or cellulose esters, particularly the acetates.

The resulting polyamide may be formed into a web by means of known melt blown or spunbond techniques. Alternatively, the polyamide may be sprayed molten or as an aqueous dispersion during other nonwoven manufacturing processes such as air laid or wet laid processes to bind fibers and impart strength.

The polyamide may be used alone or in combination with other polymers to create a variety of useful properties in the resulting web. By combining the water soluble polyamide with conventional insoluble polymers such as polyethylene, polypropylene, polyester or polyamide sequentially during the web forming process, the resulting web will have a water soluble matrix. Preferably, the insoluble polymer is applied to form a discontinuous web. The water soluble polyamide is then applied to the discontinuous regions such that the resulting web dissolves at the locations of the polyamide leaving small portions of the insoluble portions intact. Alternatively, the water soluble polyamide may be applied as a continuous phase with discontinuous regions of the insoluble polymer. This technique creates a low cost flushable web. By combining the water soluble polyamide with at least one insoluble polymer simultaneously, it is possible to create webs having hydrophilic character that do not disperse in water.

The polyamide may additionally be combined with biodegradable materials or selectively dispersible materials to create nonwoven webs having unique combinations of properties. As in the case of the more conventional polymers, depending on the method, sequences and ratios by which they were combined, the web may or may not be water dispersible. If the polyamide is added sequentially during the web forming process, each material tends to maintain its unblended properties, whereas simultaneously combining the polyamide in the melt phase with at least one other polymer results in webs with properties intermediate between the unblended polymers. The polymer present at the higher concentration tends to govern the overall properties of the nonwoven web.

Useful biodegradable polymers include those which are photodegradable, microbiologically and hydrolytically degradable, as well as cellulosics so long as the polymer can be incorporated into a web either alone or combined with a compatible carrier. Representative examples include polylactic acid, polyhydroxybutyrate, polyhydroxybutyrate-valerate, polycaprolactone, and mixtures thereof.

Selectively dispersible polymers include those which are dispersible in aqueous environment under prescribed conditions, yet are not dispersible in all aqueous environments. Examples include materials that are alkaline dispersible or saline insoluble. The Eastman AQ copolyesters, which are water dispersible yet saline insoluble are preferred for articles intended to absorb body fluids.

The invention is further illustrated by the following non-limiting examples:

EXAMPLES

Test Methods
 1. Melt Viscosity is determined in accordance with the following procedure using a Brookfield Laboratories DVII+ Viscometer in disposable aluminum sample chambers. The spindle used is a SC-27 hot-melt spindle, suitable for measuring viscosities in the range of from 10 to 100,000 centipoise. The sample is placed in the chamber, which is in turn inserted into a Brookfield Thermosel and locked into place. The sample chamber has a notch on the bottom that fits the bottom of the Brookfield Thermosel to ensure that the chamber is not allowed to turn when the spindle is inserted and spinning. The sample is heated to the desired temperature, with additional sample being added until the melted sample is about 1 inch (2.5 cm) below the top of the sample chamber. The viscometer apparatus is lowered and the spindle submerged into the sample chamber.

Lowering is continued until brackets on the viscometer align on the Thermosel. The viscometer is turned on, and set to a shear rate which leads to a torque reading in the range of 30 to 60 percent. Readings are taken every minute for about 15 minutes, or until the values stabilize, which final reading is recorded.

2. Blocking Resistance is determined by preparing a polyamide coated sheet of 20# bleached kraft paper (standard copy paper) having a polyamide thickness ranging from about 0.6 to 1 mil using a suitable coating device or draw-down technique. The polyamide coated paper is then cut into 1" strips and conditioned at 50% relative humidity for two hours. At least three strips of the polyamide coated paper are placed on a tray and a piece of uncoated paper placed on top of the polyamide sandwiching the polyamide between two paper layers. A 500 g weight is place on top of each strip resulting in a force of 500 g/sq. inch and the tray is placed in a 140° F. oven for 24 hours. After 24 hours, the uncoated paper is removed noting the extent of polyamide sticking or picking to the uncoated paper. The extend of blocking is characterized as follows:

"excellent"—no picking, paper falls from polyamide without resistance

"good"—the uncoated paper must be removed by hand and exhibits very slight picking "okay"—the uncoated paper must be removed by hand and exhibits significant picking, but no fiber tear "poor"—the uncoated paper must be removed by hand and exhibits fiber tear 3. Humidity Resistance is tested in the same manner as blocking resistance with the exception that the test is conducted at 100° F. and 90% relative humidity for 24 hours.

During the preparation of the following polyamide examples as follows the reaction conditions were maintained at a temperature of about 400° F. or as low as possible to insure the resulting polyamide is light in color.

Example 1

(NP-2116)

A water soluble polyamide was produced by reacting 39.37 parts adipic acid with 58.41 parts of TTD diamine such that the resulting polyamide had a viscosity of about 10,000 cps to about 12,000 cps at 400° F. as measured by a Brookfield viscometer. Stearic acid (Emersol-132) is utilized at concentrations of about 0.72 parts and may be employed at concentration ranging from about 0.5 −2 wt-% to control the viscosity of the resulting polyamide. The polyamide was sprayed with a Bayer and Otto hotmelt spray gun to form a nonwoven web. The polyamide was premelted at 400° F. in an oven and sprayed onto release paper while maintaining an application temperature ranging from about 390° F. to 400° F. At a pressure of about 40psi, the basis weight of the web was 72.5 g/m$^2$ whereas at a pressure of 60psi the basis weight was reduced to 33.9 g/m$^2$. The applicants surmise that nonwoven web may be formed with commercial meltdown or spunbond web forming equipment at temperatures ranging from about 375° F. to 400° F. The polyamide was also used to form a nonwoven web with J & M meltblown hot melt spray applicators at a temperature of 400° F. Both webs were readily soluble in tap water such that a 1"×1" piece will solubilize in approximately 20 minutes without agitation. The polyamide was fast setting and exhibited excellent blocking resistance at 100° F./90% RH.

Example 2

A second polyamide was produced from the same reactants as Example 1 without stearic acid such that the viscosity is about 35,000 cps at 400° F. In the absence of the chain terminator monoacid, the viscosity is nearly three times that of Example 1. The polyamide was sprayed with a Bayer and Otto hotmelt spray gun at a temperature of about 400° F. The basis weight can be adjusted with the air pressure as in Example 1. The resulting nonwoven web resembled conventional spunbond nonwoven formed from water insoluble polyester or polypropylene, yet the web is readily soluble in tap water.

Example 3

The polyamide of Example 2 was combined with a compatible water insoluble polyamide produced by reacting primarily dimer acid with ethylene diamine such that the viscosity of the water insoluble polyamide was about 58,000 cps at 400° F. The polyamides were melted and combined at a ratio of 4 parts water soluble polyamide to 1 part insoluble polyamide and at a ratio of 1 part water soluble polyamide to 4 parts water insoluble polyamide. The blended polyamides were then sprayed with a Bayer and Otto spray gun at a temperature ranging from about 410° F. to 420° F. to form a web resembling conventional meltblown or spunbond nonwoven. The web formed from 4 parts water soluble polyamide readily disperses in tap water. The web formed from 1 part water soluble polyamide is not dispersible in water, yet is hydrophilic. Therefore, blends of small concentrations of water soluble polymers with insoluble polymers are useful for imparting hydrophilicity into nonwoven webs. This is particularly useful for creating hydrophilic zones in-line for disposable absorbent products.

Example 4

An Eastman AQ copolyester having an intrinsic viscosity of about 0.2 was sprayed on both sides of the water soluble web formed in Example 1. The Eastman AQ copolyesters are soluble in water, yet saline or body fluid insoluble. The resulting web disperses in water yet is not dispersible upon submersion in saline for 45 minutes.

Example 5

The water soluble polyamide of Example 1 was sprayed simultaneously with an experimental biodegradable polymer, Eastman Polyester 14766, to form a fused nonwoven web. Upon placing the web in water, some dissolution was observed yet the web remained intact due to the presence of the polyester. This combination is particularly preferred for disposable diapers as a possible solution for solid waste management concerns. When the water soluble polyamide was combined with the Eastman Polyester 14766 sequentially, the discreet webs could be easily separated from each other. Applicants surmise the polyamide could be sprayed simultaneously with any water insoluble polymer that is suitable for web forming processes.

The water soluble webs of Examples 1 and 2 are heat fusible. Examples 3–5 may also be heat fusible, but will no longer be 100% soluble.

Comparative Example A

In order to compare the properties of the improved water soluble web of the present invention, it was compared to PVOH. Although nonwoven web comprising PVOH are known, such webs are not commercially available. Applicants attempted to create a nonwoven web with hot melt spray applications as in Examples 1–5.

Vinex 2019, PVOH commercially available from Air Products was heated at 170° C. After 30 minutes the Vinex 2019 had turned light brown due to degradation. Since the material was unflowable at 170° C., the temperature was increased to about 210° C. upon which the Vinex 2019 turned very dark in appearance and fumed. Therefore, such attempts were unsuccessful due to the poor thermal stability and processability to PVOH.

Since a nonwoven web could not be formed from PVOH without the extrusion meltblown equipment taught by Dever, Benson and Pair in the INDA publication mentioned above, the applicants formed a film from an aqueous emulsion to compare the heat seal properties. A 15% aqueous solution of Vinex 2019 and a 15% aqueous solution of the water soluble polyamide of Example 1 were used to cast films. Upon drying, the thickness of the resulting films was about 1 to 2 mils.

The films were cut into pieces and used to heat seal standard copy paper with a small iron. Table 1 depicts the results of the heat seal bonds and this demonstrates the improved properties of the water soluble polyamide with respect to PVOH.

TABLE 1

| Temperature | Time | Result |
| --- | --- | --- |
| 290–305° F. | 1 Minute | Vinex 2019 did not bond the paper. It stuck to the side which was pressed by iron but peeled off easily when cooled. No fiber tear. |
| 290–305° F. | 1 Minute or 30 Seconds | Example 1 exhibited excellent bond strength resulting in fiber tear. |
| 390–410° F. | 1 Minute | Vinex 2019 only bonded to the paper side which was directly in contact with iron, but did not bond paper on both sides. |
| 390–410° F. | 30 Seconds | Example 1 gave excellent bonds resulting in fiber tear. |

Example 7

(4962-19)

A water soluble polyamide was produced by reacting 49.03 parts adipic acid with 48.84 parts of EDR-148 diamine, 1.50 parts of Irganox 1098 and 0.59 parts of stearic acid (Emersol-132) to control the viscosity. The resulting polyamide had a viscosity of about 12,000 cps at 400° F. as measured by a Brookfield viscometer. The polyamide exhibited no blocking at 100° F./90% RH. Alternatively, this polyamide may be produced in the absence of the monoacid and then be further combined with waxes, tackifiers, crystalline polymer, and mixtures thereof as demonstrated in the following Example 8.

Example 8

(4198-5)

A water soluble polyamide was produced by reacting 395.2 g adipic acid with 292.3 g of EDR-192 diamine and 21.0 g of Naugaurd antioxidant. The resulting polyamide had a viscosity in the range of 8800 to 10,000 cps at 400° F. as measured by a Brookfield viscometer. The resulting polyamide was subsequently combined with Kenamide W-40 at concentrations of 1, 2 and 5 wt-%. The resulting blends exhibited good blocking resistance at 1 and 2 wt-% of Kenamide W-40 and very slight blocking at 5 wt-% at 100° F./90% RH.

Comparative Example B (4029-64)

A water soluble polyamide was produced by reacting 395.2 g of adipic acid with 292.3 g of EDR-192 diamine in accordance with the teachings of Speranza. The reactants are identical to inventive Example 8. The resulting polyamide had a viscosity in the range of 8800 to 10,000 cps at 400° F. as measured by a Brookfield viscometer. The polyamide was slow setting and exhibited poor blocking resistance at 100° F./90% RH.

Example 9

(5095-29)

A water soluble polyamide was produced by reacting 42.57 parts adipic acid with 55.18 parts of EDR-192 diamine, 1.48 parts of Irganox 1098 and 0.77 parts of stearic acid (Emersol-132). The resulting polyamide had a viscosity of about 4,000 cps at 400° F. as measured by a Brookfield viscometer and exhibited good blocking resistance with some blocking around the edges of the weight at 100° F./90% RH, but no fiber tear. Hence by employing a chain terminator reactant into the polyamide of Comparative Example B, the blocking resistance is greatly improved.

Comparative Example C (4029-75)

A water soluble polyamide was produced by reacting 146.1 g of adipic acid, 143.1 dimer acid with 192.0 g of EDR-192 diamine, 150 g of ED-600, 9.5 g of Irganox 1098, and 0.4 g of Dow DB100 antifoaming agent in accordance with the teachings of Speranza. The resulting polyamide had a viscosity of about 39,000 cps at 400° F. as measured by a Brookfield viscometer. The polyamide was slow setting and blocked at 100° F./90% RH.

Example 10

(4198-2)

Comparative Example C was further blended with Kenamide W-20 wax at concentrations of 1, 2 and 5 wt-%. The resulting blends exhibited good blocking resistance.

Comparative Example D (4198-22)

A water soluble polyamide was produced by reacting 164.4 g of adipic acid, 71.3 g of azelaic acid, 205.8 g of EDR-148 diamine, 61.8 g of Jeffamine® D-400, and 7.5 g of Irganox 1098 in accordance with the teachings of Speranza. The resulting polyamide had a viscosity of about 5700 cps at 400° F. as measured by a Brookfield viscometer. The polyamide was slow setting and blocked at 100° F./90% RH.

Example 11

(4198-28 & 29)

Comparative Example D was further blended with Kenamide W-40 wax at a concentration of 4 wt-%. The resulting blend exhibited good blocking resistance and the wax component had no measurable effect on the solubility/dispersibility in standard repulpability tests.

Comparative Example E
(4962-56)

A water soluble polyamide was produced by reacting adipic acid, EDR-148 diamine, and Jeffamine® D-230, and 7.5 g of Irganox 1098 in accordance with the teachings of Speranza. The resulting polyamide had a viscosity of about 2100 cps at 350° F. as measured by a Brookfield viscometer. The polyamide is tacky and slow setting.

Example 12
(4962-56)

Comparative Example E was further blended with Kenamide W-40 wax at a concentration of 5 wt-%. The resulting blend was fast setting and non-blocking.

We claim:

1. A nonwoven web comprising at least one water soluble polyether amide selected from the group consisting of:
   a) the reaction product of at least one dicarboxylic acid or an ester thereof, with polyalkylene glycol diamine having the formula:

$$NH_2-(CH_2)_3-(OCH_2-CH_2)_2-O-(CH_2)_3-NH_2;$$

b) the reaction product of polyalkylene glycol diamine with at least one dicarboxylic acid or an ester thereof, and at least one monocarboxylic acid, said polyalkylene glycol diamine having the formula:

$$NH_2-(CH_2)_x-(OCH_2-CH_2)_y-O-(CH_2)_x-NH_2$$

wherein X ranges from 2 to 3 and Y ranges from 1 to 2;

c) up to about 95 wt-% of the reaction product of at least one polyalkylene glycol diamine with at least one dicarboxylic acid or an ester thereof, said polyalkylene glycol diamine having the formula:

$$NH_2-(CH_2)_x-(OCH_2-CH_2)_y-O-(CH_2)_x-NH_2$$

wherein X ranges from 2 to 3 and Y ranges from 1 to 2; and at least one ingredient selected from the group consisting of waxes, tackifiers, crystalline polymers, monocarboxylic acids and mixtures thereof.

2. The nonwoven web of claim 1 further comprising at least one polymer selected from the group consisting of a biodegradable polymer, a water insoluble polymer and a selectively dispersible polymer.

3. The nonwoven web of claim 2 wherein said biodegradable polymer is selected from the group consisting of polylactic acid, polyhydroxybutyrate, polyhydroxybutyrate-valerate, polycaprolactone, and mixtures thereof.

4. The nonwoven web of claim 2 wherein the water insoluble polymer is selected from the group consisting of polyethylene, polypropylene, polyester, polyamide and mixtures thereof.

5. The nonwoven web of claim 1 wherein said web is heat fusible.

6. A disposable absorbent article comprising the nonwoven web of claim 1.

7. A disposable absorbent article comprising the nonwoven web of claim 2.

8. The article of claim 6 wherein said article is selected from the group consisting of disposable diapers, feminine napkins, surgical gowns, bed pads, and incontinent devices.

9. The article of claim 7 wherein said article is selected from the group consisting of disposable diapers, feminine napkins, surgical gowns, bed pads, and incontinent devices.

10. A flushable, disposable article comprising the nonwoven web of claim 1 wherein portions of the least one water soluble polyamide and portions of the water insoluble polymer are in contact with each other.

11. A flushable, disposable article of claim 10 wherein said water soluble polyamide portions form a continuous matrix.

12. A flushable, disposable article of claim 10 wherein said water soluble polyamide portions substantially surrounds said water-insoluble polymer portions.

13. A water soluble web comprising at least one polyether amide which is the reaction product of at least one dicarboxylic acid or an ester thereof, with polyalkylene glycol diamine having the formula:

$$NH_2-(CH_2)_3-(OCH_2-CH_2)_2-O-(CH_2)_3-NH_2.$$

14. A water soluble web comprising at least one polyether amide which is the reaction product of polyalkylene glycol diamine with at least one dicarboxylic acid or an ester thereof, and at least one monocarboxylic acid, said polyalkylene glycol diamine having the formula:

$$NH_2-(CH_2)_x-(OCH_2-CH_2)_y-O-(CH_2)_x-NH_2$$

wherein X ranges from 2 to 3 and Y ranges from 1 to 2.

15. A water soluble web comprising up to about 99 wt-% at least one polyether amide which is the reaction product of at least one polyalkylene glycol diamine with at least one dicarboxylic acid or an ester thereof, said polyalkylene glycol diamine having the formula:

$$NH_2-(CH_2)_x-(OCH_2-CH_2)_y-O-(CH_2)_x-NH_2$$

wherein X ranges from 2 to 3 and Y ranges from 1 to 2; and at least one ingredient selected from the group consisting of waxes, tackifiers, crystalline polymers, monocarboxylic acids and mixtures thereof.

16. The nonwoven web of claim 1 wherein said web is non-blocking.

17. The nonwoven web of claim 1 wherein said web is humidity resistant.

* * * * *